United States Patent [19]

Runge

[11] Patent Number: 4,485,093

[45] Date of Patent: Nov. 27, 1984

[54] IMMUNOTOXIN CONJUGATE WHICH COMPRISES ARSANILIC ACID, USEFUL FOR TREATING MALIGNANT TUMORS, PARTICULARLY PANCREATIC CANCER

[76] Inventor: Richard G. Runge, 6311 S. 149th St., Omaha, Nebr. 68137

[21] Appl. No.: 408,041

[22] Filed: Aug. 13, 1982

[51] Int. Cl.³ .................... A61K 39/00; A61K 45/02; A23J 0/00; C07G 7/00
[52] U.S. Cl. ....................................... 424/85; 424/88; 260/112 B; 260/112 R
[58] Field of Search ....................... 436/518, 523, 532; 260/112 B, 112 R, 6; 424/85, 177, 86, 88

[56] References Cited

U.S. PATENT DOCUMENTS

| | | | |
|---|---|---|---|
| 4,033,819 | 7/1977 | Helting | 195/29 |
| 4,046,722 | 9/1977 | Rowland | 260/6 |
| 4,340,535 | 7/1982 | Voisin et al. | 260/112 B |
| 4,359,457 | 11/1982 | Neville, Jr. et al. | 424/85 |
| 4,368,149 | 1/1983 | Masuho et al. | 260/112 B |
| 4,440,747 | 4/1984 | Neville, Jr. et al. | 424/85 |

Primary Examiner—Thomas G. Wiseman
Assistant Examiner—Robin Teskin
Attorney, Agent, or Firm—Zarley, McKee, Thomte, Voorhees & Sease

[57] ABSTRACT

An immunotoxin conjugate, useful for treating malignant tumors in mammals, which consists of arsanilic acid and tumor specific antibodies covalently bound to a polyglutamic acid linking agent is taught. The conjugate selectively delivers arsanilic acid to a tumor, killing the tumor cells and exhibiting little or no toxicity to normal cells. The conjugate is effective in treating human pancreatic cancer.

8 Claims, No Drawings

IMMUNOTOXIN CONJUGATE WHICH COMPRISES ARSANILIC ACID, USEFUL FOR TREATING MALIGNANT TUMORS, PARTICULARLY PANCREATIC CANCER

BACKGROUND OF THE INVENTION

From time to time in the past, there have been efforts made to suppress tumor growth by using cytotoxic drugs linked to tumor specific antibodies as a form of cancer chemotherapy. The theory is that the antibodies would selectively transport, or deliver, the drug to the target tumor site where the cytotoxic agent would kill the tumor. However, in actual practice, it has been found that it frequently occurs that if tumor specific antibodies are linked to cytotoxic drugs, either the activity of the drug is hindered, or the activity of the antibody is hindered, or both are hindered. Thus, the net effect of the linking, or bonding of the two agents together, is that neither is fully effective.

In addition, it has been found that many of the products obtained by a direct bonding, or linkage, between a cytotoxic drug and tumor specific antibodies, results in the formation of compositions of matter which are pharmaceutically unacceptable in that they are insoluble in traditional pharmaceutical diluents, making the actual use of the composition in treatments, particularly parenteral injections, difficult if not impossible.

Additionally, in the past, attempts at linkage of cytotoxic drugs to tumor specific antibodies, have encountered difficulties in selection of the cytotoxic agent. In order to have a successful and useful composition, one must select a cytotoxic agent which is relatively non-toxic when bound or linked, but only becomes toxic in its free form after transport to the site of the malignant tumor, presumably where enzymes digest a portion of the molecule releasing the toxic agent to kill the tumor.

For examples of bonding of cytotoxic agents directly to antibodies, see Miner, et al., U.S. Pat. No. 3,803,302, Sela, U.S. Pat. No. 4,093,607, and Yoshikumi, U.S. Pat. No. 4,315,851. For an example of indirect linkage, that is, where the cytotoxic drug and the tumor specific antibody are linked, but not directly linked to each other, that is linked through an intermediate molecule, see Rowland, et al. (1975), *Suppression of Tumor Growth in Mice By a Drug Antibody Conjugate Using a Novel Approach to Linkage.* Nature 255:487–488. However, as heretofore mentioned, the direct linkage approach of the cited United States Letters Patents, inherently involves problems because of the strong likelihood of decreased effectiveness of either the tumor specific antibody, or the cytotoxic agent, or both. The indirect technique of Rowland et al. employs p-phenylenediamine mustard as the cytotoxic drug. The results he achieves show inconsistency, some difficulty in obtaining binding of the drug to intermediate carrier, and demonstrates results only in tissue cultures.

In contrast to the prior art, and the problems of the prior art mentioned above, the applicant has discovered a linking technique in combination with a specific cytotoxic amine agent, which when employed, allows a tumor specific antibody and the cytotoxic amine-containing agent to be indirectly linked together by both being linked to a common carrier, without being specifically linked to each other. The result is that the tumor specific activity of the antibody and the pharmacological activity of the cytotoxic amine-containing agent are not interferred with in any significant manner by the presence of the other agent, or the presence of the linked carrier. Also, in contrast to the Rowland technique, the present invention utilizes a cytotoxic agent which is easy to work with, is commonly available, and, when employed in the present invention, shows definite positive results in living organisms as opposed to mere tissue culture testing.

It is therefore a primary objective of the present invention to provide an immunochemotherapy process and composition which is effective against malignant tumors.

Another object of the present invention is to provide an immunochemotherapy composition which is water soluble, which has a cytotoxic amine-containing agent, and a tumor specific antibody, both linked to a common carrier molecule without each of the agents being linked directly to each other, such that they are both freely available; that is, the antibody and the cytotoxic amine are available each to provide their specific activity, but each without interference from the other.

An additional specific object of the present invention is to provide an immunochemotherapy composition which employs arsanalic acid as the cytotoxic amine-containing agent.

A still further objective of the present invention is to provide a carrier molecule which is capable of reacting with arsanilic acid as the cytotoxic amine-containing agent, and also capable of reacting with a tumor specific antibody, such that both can be linked to the carrier molecule to provide a composition of matter which is water soluble.

A yet further objective of the present invention is to provide a composition of matter which is capable of parenteral injection (i.e., intravenous, intraperitoneal, intralesional) to allow delivery of a cytotoxic agent to a malignant tumor site.

Another objective of the present invention is to provide a method and manner in which arsanilic acid may be linked as a cytotoxic amine-containing agent to a water soluble intermediate carrier molecule which is the reaction product of polyglutamic acid and a carbodiimide.

Still another objective is to provide an indirect linking of toxic agent and antibody so that larger amounts of toxic agent can be bound per antibody molecule, without affecting antibody activity.

A still further objective of the present invention is to provide a method for delivering to a specific tumor site of a host organism, a cytotoxic drug agent in a manner in which the agent appears to be relatively non-toxic during transport or delivery, and primarily becomes toxic at the malignant tumor site.

The method and manner of accomplishing each of the above objectives, as well as others, will be apparent to those skilled in the art from the detailed description of the invention which follows hereinafter.

SUMMARY OF THE INVENTION

An immunochemotherapy composition characterized by a water soluble intermediate carrier to which a cytotoxic amine agent, preferably arsanilic acid is linked, and to which a specific tumor antibody is also linked, without each being linked directly to the other. The water soluble carrier is preferably a reaction product of polyglutamic acid with a carbodiimide, with the carbodiimide reaction being first employed to activate carboxyl groups of the polyglutamic acid. After actuation, they will in turn react, displacing the carbodiimide as a leaving group and attaching through a peptide linkage the arsanilic acid cytotoxic agent to the polyglutamic acid. Other unreacted carboxyl group sites are then reacted with the tumor specific antibody, providing a water soluble composition. The water soluble composition can be used in a pharmaceutical diluent such as saline solution to provide parenteral injections (i.e., intravenous, intraperitoneal, intralesional).

DETAILED DESCRIPTION OF THE INVENTION

In accordance with the present invention, which involves linkage of a tumor specific antibody and a cytotoxic amine-containing agent, preferably arsanilic acid, to an intermediate carrier, as opposed to linkage to each other, there is a minimization of interference with the chemical structure of either the tumor specific antibody or the cytotoxic agent. As a result, the produced composition has little or no loss of activity of either the antibody or the drug.

As is known to those skilled in the art, malignant tumors produce antigens. The response of immunocompetent organisms (or hybridoma cells) to the antigen is production of antibodies. These antibodies, if isolated and then returned to the host organism will freely transport themselves directly to the antigen. In other words, they are specific to the antigen which caused the antibody formation in the first place. In accordance with this invention, antibodies produced by immunocompetent organisms or hybridoma cells to malignant tumors are isolated and thereafter used as a method to specifically deliver a cytotoxic agent to the target tumor cell site.

The method and manner of isolating antibodies is well known and is not a part of this invention. Indeed, many antibodies are freely commercially available. However, for the sake of completeness of the present invention description, the antibodies which were employed were obtained by injecting purified porcine gastric mucin into a rabbit. Three injections were provided, one per week for three weeks. Seven weeks after the first injection, the animal was bled to obtain the serum containing the antibody. Further details will be shown in the example. Again, it is not important how one collects the antibody, that being well within the skill of the art. Monoclonal antibodies may also be used. The antibody isolated from the rabbit as mentioned above, is a monospecific anti-A antibody and known to be tumor specific for pancreatic cancers in Syrian hamsters.

As heretofore mentioned, the cytotoxic agent, or drug, used in this invention is a cytotoxic amine-containing agent. It is highly preferred and in some cases critical that the agent be arsanilic acid. It is, however, conceivable that in accordance with the technique of this invention, other cytotoxic agents (containing amine groups) selected from known drugs may be employed, including alkylating agents, antimetabolites, antibiotics and alkaloids. Exemplary anti-tumor drugs embraced by these classes include daunomycin, adriamycin, methotrexate, mitomycin, cytosine arabinoside and 6-azauridine. These drugs are described in "The Pharmacological Basis of Therapeutics", edited by Goodman, et al., 5th Ed. Section XV, pages 1248 to 1308, 1975, published by the Macmillan Co., New York. In operation, the drug will be used in an amount that contains sufficient drug to elicit the desired pharmacological response. Generally, this amount will correspond to the amount disclosed in the above text for the respective drug, which is incorporated herein by reference.

As earlier mentioned, the preferred cytotoxic amine agent is arsanilic acid which is freely and openly available commercially. Arsanilic acid is preferred for use in this invention because of several factors. First, it can be essentially detoxified when reacted with the intermediate carrier as discussed below. Secondly, it provides a composition of matter when reacted with the intermediate carrier which is water soluble, and thus pharmacologically acceptable and easy to work with. Third, when arsanilic acid is used as a cytotoxic amine-containing agent for use in this invention, it does not alter the activity of the antibody in any significant degree. Thus, the antibody freely directs the composition to the tumor site. Fourth, as indicated in the examples below, it has demonstrated pharmacological efficacy in killing tumors in host organisms.

Now having selected both the tumor specific antibody and the cytotoxic amine-containing agent, the next objective becomes linking the two of them together in a manner in which they are not directly linked to each other so that they will not interfere with each other's activity; and linking in a manner which will provide a water soluble composition which is pharmaceutically acceptable for parenteral injection.

The carrier molecule must be a water soluble organic polymer carrier with multi-reactive sites. Generally, the multi-reactive sites are manifested by a plurality of functional groups, particularly carboxylic acid groups. The preferred compound for use is polyglutamic acid. The molecular weight of the polyglutamic acid, which is freely commercially available, may vary from 2,000 to 35,000, with from 4,000 to 15,000 being preferred. Within the preferred range, there are from approximately 30 to 100 glutamic acid residues per chain. Very satisfactory results for this invention are achieved with an approximate polyglutamic acid molecular weight of 10,000.

It has, however, been found that arsanilic acid will not directly react with the carboxyl groups of polyglutamic acid. Thus, the multi-reactive sites, that is, the carboxyl groups of the polyglutamic acid, must first be activated. In accordance with this invention, they can be activated, such that they will later react with arsanilic acid, by first reacting those with a carbodiimide, to form an active water soluble carrier product. Carbodiimides are a well-known class of compounds, having the general formula: $R-N=C=N-R'$ wherein R and R' in the general carbodiimide formula represent any alkyl, aryl or allyl group, which is essentially non-reactive and does not interfere with water solubility of the resulting compound or itself provide competing reactive sites. Generally, it is preferred that R and R' be unsubstituted lower chain alkyl groups, whether branched or straight chain. Lower alkyl as used herein, means $C_1$ to 12.

The preferred carbodiimide for use in this invention, although it is not in any sense critical, is 1-ethyl-3(3-dimethylaminopropyl) carbodiimide, hereinafter abbreviated "EDC".

The reaction between the carbodiimide and the polyglutamic acid is carried out at room temperature and is a simple addition reaction wherein the carbodiimide adds to the carboxyl group. The carbodiimide can be thought of as "activating" the carboxyl group of the polycarboxylic acid, that is, polyglutamic acid, such that it is now a reactive site for the cytotoxic agent, particularly arsanilic acid. Thus, the carbodiimide is merely an intermediate activating composition which is a "leaving group". The reaction with cytotoxic amine-containing agents is a direct addition reaction, can be carried out at room temperature and results in a carboxy amide bond involving the free carboxyl groups of the polyglutamic acid and the free amino groups of the toxic agents. The reaction occurs in a short period of time, and has been noted to be substantially complete in as short as five minutes, for small reaction quantities.

After the activation of the carboxylic acid sites of the polyglutamic acid, they are now ready for reaction with the cytotoxic amine-containing agent, particularly arsanilic acid. Arsanilic acid, preferably in a stoichiometric excess to assure complete addition, is then added to the polyglutamic acid carbodiimide active intermediate, with the result being that the carbodiimide group leaves and the arsanilic acid adds at the leaving group sites to form a carboxy amide or peptide linkage between the amine group of the arsanilic acid and the carboxylic acid group of the polyglutamic acid. Thus, the arsonate group is left free and uninterferred with by the reaction. The reaction between the polyglutamic acid-carbodiimide active water soluble carrier and the arsanilic acid to provide an intermediate conjugate having the arsanilic acid attached to the carrier molecule, does not appear to be process critical. In experimental runs, it has been shown that the reaction is again a simple substitution reaction wherein the arsanilic acid, through the peptide linkage, is substituted for the leaving carbodiimide group. It is not temperature dependent, nor does it appear to be time critical. In reaction runs, as demonstrated in the examples, it has been allowed to react for up to three hours at room temperature to assure reaction completion.

In accordance with the next step of the process of this invention the composition, which in its present state is referred to herein as the "intermediate conjugate", now has the cytotoxic amine-containing agent attached to it. It yet needs to have the tumor specific antibody attached to it, without also attaching the antibody to the arsanilic acid portion of the molecule.

It will be recalled that the polyglutamic acid has many carboxylic acid sites, only some of which have reacted with the arsanilic acid. Thus, there are additional reactive sites which remain on the carrier molecule for reaction with the antibody.

Of course, as each step of the reaction is accomplished, as those skilled in the art will understand, excessive quantities of unreacted ingredients are removed by conventional techniques. Those need not be described in detail herein, but will be left for specific demonstration in the examples which follow hereinafter.

Turning now to the reaction between the intermediate conjugate having the arsanilic acid attached thereto, and the tumor specific antibody. Again, to assure that the remaining carboxylic acid groups of the polyglutamic acid are sufficiently reactive to react with the antibody, carbodiimide activator, as previously discussed, is added. Carbodiimide, preferably EDC, functions in the exact manner as previously discussed. After the carbodiimide is allowed to react for about five minutes, the reaction mixture may be diluted with, for example, phosphate buffered saline solution (PBS), and purified antibody is added. Again, the reaction does not appear to be time or temperature dependent.

As demonstrated in the examples below, the only important process criteria in the antibody addition reaction, is that the reaction mixture be allowed reactive contact for a sufficient period of time to allow carbodiimide groups to leave and be replaced with the peptide linkage between free amine moieties of the antibody and carboxyl groups of the polyglutamic acid. In laboratory experiments, three hours at room temperature has been sufficient.

After the reaction is complete, the excess carbodiimide may be quenched with sodium acetate, and the mixture dialyzed to separate low molecular weight reactants from the linked product which has bound to it both the antibody and the arsanilic acid, without either of them being directly bonded to the other. For purposes of illustration, graphically what is happening can be demonstrated as follows, wherein "AB" represents antibody and "AS" represents arsanilic acid.

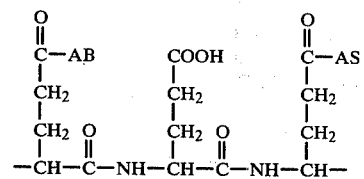

Thus, it can be seen that the antibody is attached to a carboxylic group of the polyglutamic acid, and the arsonate is likewise attached to a carboxylic moiety of the polyglutamic acid, but each to different carboxylic moieties such that they are not attached to each other. They are, however, "indirectly linked" through the polyglutamic acid molecule.

In this manner, numerous arsanilic acid molecules may be attached without significantly affecting antibody activity, as opposed to direct-linkage methods.

The linked product previously discussed, after separation and concentration, is now available for use in parenteral injection (i.e., intravenous, intraperitoneal, intralesional) treatment of tumors. For purposes of convenience, storage and shipment, it may be lyophilized if desired, and later reconstituted with pH adjusted phosphate buffered saline (PBS). The dose administered of the composition, or linked product, will vary with the particular tumor, its severity and the weight and size of the host animal. However, for the hamster studies discussed in the examples below, the dosage was generally 5 milligrams of linked product. For individual human dosages, it would normally be expected to have a dosage range of from 10 to 50 milligrams per kilogram of body weight which should be well, under the $LD_{50}$. The composition may be administered in aqueous solution, or also incorporated into particulate carriers, such as liposomes. With regard to the time of treatment, it has been found that a series of parenteral injections over a several week period provides the most effective treatment, particularly for pancreatic cancers.

EXAMPLES

The following examples are offered to further illustrate, but not limit, the process of this invention. In each of the examples, the linked product, that is, the conjugate as graphically illustrated above, which has a polyglutamic acid backbone with some of the carboxylic groups reacted with arsanilic acid, and some other portion of the carboxylic acid groups of the polyglutamic acid reacted with the tumor specific antibody, is prepared in the following manner.

Monospecific, anti-A antibodies can be obtained commercially from Chembiomed, Ltd. of Edmonton, Alberta. However, for the specific examples used below, they were prepared by injecting purified porcine gastric mucin into a rabbit. Three injections were provided separately, one per week for three weeks. Seven weeks after the first injection the animal was sacrificed to obtain the serum. This serum had the anti-A antibodies. The anti-A-antibodies were purified by affinity chromatography, using Synsorb A manufactured by Chembiomed. This adsorbent consists of a pure, synthetic, trisaccharide A-substance covalently bound to silica. Anti-A rabbit antiserum is placed on an adsorbent-packed column and the anti-A antibodies attach to the bound antigen. The remaining protein is removed with phosphate buffered saline. The bound antibodies are then eluted with 1.5% $NH_4OH$ in saline, giving purified (monospecific)anti-A antibodies. The eluate is immediately neutralized with 3M monobasic sodium phosphate. The antibodies are concentrated to 1 mg/ml and stabilized with 0.1% Bovine Serum Albumin (BSA).

The antibody is then set aside for the moment. Next, polyglutamic acid (80 milligrams) is dissolved in 10 milliliters of a saline solution, and 320 milligrams of EDC are added and the mixture is allowed to react at room temperature for five minutes. Thereafter, 4.8 milliliters of concentrated arsanilic acid solution is prepared by dissolving up to 150 mg of arsanilic acid per ml of 1 normal sodium hydroxide. 4.8 milliliters of this solution are added to the reaction mixture which is allowed to continue reacting for three hours at room temperature. The amount of arsanilic acid added is in excess of the stoichiometric amount.

Next, excess unreacted arsanilic acid,, and carbodiimide are removed by dialysis against a phosphate buffered saline solution. This removes the small molecular weight compounds leaving behind only the polyglutamic acid-arsanilic acid conjugate. Dialysis is accomplished by pouring the solution, (particularly in the instance described herein approximately 16 milliliters) into a dialysis bag and placing this into 2-3 liters of PBS. The low molecular weight compounds pass through the membrane in 24 hours leaving behind only the desired product which is then removed.

Thereafter, the intermediate just described is now ready to form the final linked product by adding the previously described anti-A, antibody. To approximately 20 milliliters of the arsanilic acid-polyglutamic acid intermediate carrier are added 80 milligrams of carbodiimide and they are reacted at room temperature for five minutes. The reaction mixture is then diluted with an additional 20 milliliters of PBS and 60 milliliters of diluted purified anti-A antibody, as previously described, are added. (Approximately 20 milligrams of purified antibody is present in this solution). The reaction is allowed to continue for three hours at room temperature after which one gram of sodium acetate is added to quench the excess carbodiimide. The reaction mixture is then dialyzed against five liters of PBS for 24 hours. The final linked product, or conjugate, is then concentrated down to one milligram per milliliter of antibody protein by membrane ultra-filtration, and stabilized with 0.1% BSA. Some portions of it were freeze dried and later reconstituted with pH adjusted PBS (pH 7.2). Thereafter, the immunologic reactivity of the linked product was studied as described below.

Malignant growths were induced in hamsters by treatment with a known carcinogen causing pancreatic cancer, hereinafter referred to as BOP, whose technical name is N-nitrosobis (2-oxopropyl) amine. Fourteen hamsters were treated with a total of 80 mg/kg of BOP over a four week period. Thirty weeks after their last BOP injection, eight animals were treated i.p. (intraperitoneally) with 5 mg of monospecific anti-A to which arsanilic acid (via PGA) had been conjugated (i.e., 1 mg AA/5 mg anti-A). This represents about 1/10 of the $LD_{50}$ of unbound arsanilic acid (AA). Four animals were killed four days after injection. The pancreases were removed and thoroughly examined histopathologically (step sections). None of the animals appeared to have systemic toxic effects but because the liver is known to concentrate arsenic following exposure and to develop fatty infiltration and necrosis, it was examined also and found to be histologically unremarkable. Four animals were killed ten days after injection of conjugate. Two age-and sex-matched groups of two animals were treated with 1 mg of AA alone, and 5 mg of anti-A alone. These animals were killed one week after injection and examined in a fashion identical to that of the conjugate-treated animals. Two animals received only BOP.

Four days after injection of the conjugate there was marked acute inflammation and necrosis in the BOP-induced pancreatic growth alterations. Pancreatic ductules which exhibited dysplastic changes or what appeared to be in situ malignant changes were particularly affected. These lesions were surrounded by an intense acute inflammatory infiltrate which extended into the neoplastic epithelium itself. Some tumor cells were undergoing necrosis or were frankly necrotic. The periphery of established adenocarcinomas exhibited focal areas with similar changes; however, all of these larger tumors showed residual viable malignant epithelium, particularly in their central portions. Animals examined ten days after injection of the conjugate exhibited a similar histologic pattern; however, mononuclear elements were present in the inflammatory infiltrate (plasma cells and histiocytes) and tumor cell necrosis was more extensive. In both groups of animals, the morphologically normal ductules and larger ducts appeared unaffected, as did the benign ductular adenomas. The acinar cells and islets were also histologically unremarkable.

The animals treated with arsanilic acid alone or anti-A alone showed extensive ductular dysplastic and in situ malignant changes, as well as invasive adenocarcinomas, and were essentially indistinguishable from the BOP-treated controls. None of them exhibited the inflammatory or necrotic changes seen in the conjugate-treated animals. The livers of all of the animals were grossly and microscopically unremarkable.

This preliminary testing study showed that the BOP did indeed induce pancreatic malignant tumors, and, that the conjugate or linked product, the two terms being used interchangeably herein, was effective at being target specific from the standpoint that it was indeed delivered to the tumor site, and that the arsanilic acid cytotoxic amine agent did indeed significantly reduce the tumor, and in some cases, eradicated it. Further studies were continued.

Five groups of 5 eight-week old male Eppley colony Syrian golden hamsters were given 20 mg/kg of BOP weekly for four weeks (total 80 mg/kg). Eight weeks after the last BOP injection the first group of five animals was treated intraperitoneally with 5 mg. of monospecific anti-A antibody to which had been conjugated one-tenth of the $LD_{50}$ of arsanilic acid (1 mg). Eleven weeks after their last BOP injection, the second group of five animals was treated in exactly the same fashion. This regimen was repeated with a three-week periodicity until the final group was treated 20 weeks after their last BOP injection. The first four groups received only one conjugate treatment, whereas the final group received three conjugate injections separated by one week intervals.

The age and sex-matched controls consisted of a group of five animals who received 5 mg of anti-A antibody alone followed by 1 mg of arsanilic acid (AA) 24 hours later. This group was treated 20 weeks after their last BOP injection. Another group of five animals received BOP injections only. A third group of 5 non-BOP-treated controls received the same dose of anti-A-PGA-AA conjugate as the BOP-treated animals (single injection). All test and control animals were sacrificed at approximately the same time (23 weeks after the final BOP injection) and a complete autopsy with histopathologic examination performed.

Binding data indicated that about 60% of the available carboxyl groups of PGA (polyglutamic acid) were substituted with AA (arsanilic acid), and about 3–4 of these PGA-AA conjugates bound to each antibody molecule. With MW 10,000 PGA this amounted to about 175 AA molecules per antibody. The fall in hemeagglutination titer of type A red blood cells after conjugation of the antibody was from 1/512 to 1/256.

Under these conditions approximately 1 mg of AA could be bound to 5 mg of affinity chromatography purified anti-A antibody and the conjugate retained most of its immunologic reactivity. This dose represents about 1/10 of the $LD_{50}$ of unbound AA for each animal with each injection.

The distribution of BOP induced growth alterations in test and control animals is outlined in Table I shown directly below:

malignant lesions appears to correlate with length of survival after conjugate treatment. These animals received multiple doses of BOP, and could have developed additional lesions in the post-conjugate-treatment period. In all groups, the morphologically normal ductules and larger ducts appeared unaffected, as did the benign ductular adenomas. The acinar cells and islets were also histologically unremarkable.

A total of four adenocarcinomas were found in the groups receiving a single conjugate injection. Three of these tumors demonstrated considerable necrotic and inflammatory changes at their peripheral margins. The central portion of all of these lesions, however, showed residual viable tumor. One of the tumors showed no evidence of inhibition or destruction. It is possible that the mucin produced by this lesion was not of A blood group antigenic specificity.

Two animals in the group which received multiple injections of conjugate had invasive ductular adenocarcinomas in the splenic lobe. One lesion exhibited apparent total necrosis of the malignant glandular epitheleium with infiltration of the necrotic glands by tissue macrophages and acute inflammatory cells. In some areas infiltration of devitalized tumor cells by neutrophils could still be seen. In other areas all that remained was the histiocytic infiltrate with no identifiable tumor cells present, necrotic or viable. Step sections revealed that all areas of the tumor were similar. The other tumor in this group showed marked peripheral inflammation and necrosis, but viable tumor remained in its central portion.

The animals treated with anti-A alone followed by AA 24 hours later showed extensive ductular dysplastic and in situ malignant changes, as well as one invasive adenocarcinoma. They were essentially indistinguishable from the BOP-treated controls (Table I). None of them exhibited the inflammatory or necrotic changes seen in the conjugate-treated animals. The control

TABLE I

| Ductular Growth Alterations | Distribution of BOP-induced growth alterations in the various groups (5 animals/group) | | | | | | | |
|---|---|---|---|---|---|---|---|---|
| | Group 1 | Group 2 | Group 3 | Group 4 | Group 5 | BOP Treated Controls | Controls Treated with AA and Anti-A Separately | Conjugate Treated Controls |
| a. Adenoma | 5 | 5 | 5 | 5 | 5 | 5 | 5 | 1 |
| b. Dysplasia | 5 | 5 | 4 | 2 | 1 | 5 | 5 | 0 |
| c. Carcinoma in situ | 3 | 1 | 1 | 0 | 1 | 4 | 3 | 0 |
| d. Adenocarcinoma | 1 | 0 | 2 | 1 | 2 | 1 | 1 | 0 |
| Ductal Hyperplasia or Dysplasia | 0 | 0 | 0 | 1 | 0 | 1 | 0 | 0 |

Group 1: One conjugate treatment 8 weeks after final BOP injection.
Group 2: One conjugate treatment 11 weeks after final BOP injection.
Group 3: One conjugate treatment 14 weeks after final BOP injection.
Group 4: One conjugate treatment 17 weeks after final BOP injection.
Group 5: Three conjugate treatments 20, 21, 22 weeks after final BOP injection.
Animals in Group 5 received three weekly treatments of conjugate and were sacrificed one week after the final treatment.
Animals in all groups were sacrificed 23 weeks after final BOP injection.

The tumor bearing test animals that had received only one injection of conjugate exhibited a histologic pattern in dysplastic and in situ malignant ductules similar to that described above. However, mononuclear elements predominated in the peripery of the inflammatory infiltrate (plasma cells and histiocytes) and areas of fibrosis were present. This would be expected because of the longer time period between conjugate treatment and the time the animals were sacrificed. The number of dysplastic (pre-malignant growth alteration) and in situ group that was treated with conjugate but had not received prior BOP treatment showed no evidence of inflammation or necrosis in the pancreatic duct system, acinar cells or islets.

Also examined were the non-target tissues from all groups to determine the nature and extent of possible non-specific toxicity. Particular attention was paid to tissues known to be affected by arsenic (liver, kidney, bone marrow, brain). None of the conjugate-treated test or control animals in the study demonstrated toxic changes in non-target tissue by histopathologic examination.

The results of the testing discussed above show significant effectiveness and show that both the tumor specific antibody and the cytotoxic agent are each independently allowed to act but are carried cooperatively in such a manner that neither significantly interferes with the activities of the other. Also, the specific toxicity for tumor tissue of the conjugate is readily demonstrated by the results in these examples.

It therefore can be seen that the invention accomplishes at least all of its stated objectives.

What is claimed is:

1. A water soluble immunotoxin conjugate consisting of arsanilic acid, polyglutamic acid, and a tumor specific antibody wherein: (1) polyglutamic acid having a molecular weight from about 2,000 to about 35,000 covalently binds the antibody and the arsanilic acid via carboxyl groups on the polyglutamic acid: and (2) the arsanilic acid is present in a tumor toxic amount.

2. The immunotoxin conjugate of claim 1 wherein the polyglutamic acid has a molecular weight from about 4,000 to about 15,000.

3. The immunotoxin conjugate of claim 1 wherein said carboxyl groups on the polyglutamic acid are activated by reaction with a carbodiimide prior to binding with arsanilic acid and prior to binding with the tumor specific antibody respectively.

4. The immunotoxin conjugate of claim 3 wherein the carbodiimide is 1-ethyl-3(3-dimethyl aminopropyl) carbodiimide.

5. A method of treating tumors in mammals comprising parenterally administering to the mammal a tumor toxic effective amount of a watersoluble immunotoxin conjugate consisting of arsanilic acid, polyglutamic acid, and a tumor specific antibody wherein: (1) polyglutamic acid having a molecular weight from about 2,000 to about 35,000 covalently binds the antibody and the arsanilic acid via carboxyl groups on the polyglutamic acid and (2) the arsanilic acid is present in a tumor toxic amount.

6. The method of claim 5 wherein the polyglutamic acid has a molecular weight from about 4,000 to about 15,000.

7. The method of claim 5 wherein said carboxyl groups on the polyglutamic acid are activated by reaction with a carbodiimide prior to binding with the arsanilic acid and prior to binding with the tumor specific antibody respectively.

8. The method of claim 7 wherein the carbodiimide is 1-ethyl-3(3-dimethyl aminopropyl) carbodiimide.

* * * * *